(12) United States Patent
Kikuchi et al.

(10) Patent No.: US 6,397,660 B1
(45) Date of Patent: Jun. 4, 2002

(54) GAS ANALYZING APPARATUS

(75) Inventors: Tsutomu Kikuchi; Akira Nishina; Tetsuya Kimijima, all of Tokyo (JP)

(73) Assignee: Nippon Sanso Corporation, Tokyo (JP)

( * ) Notice: Subject to any disclaimer, the term of this patent is extended or adjusted under 35 U.S.C. 154(b) by 0 days.

(21) Appl. No.: 09/774,730

(22) Filed: Jan. 31, 2001

(30) Foreign Application Priority Data

Nov. 24, 2000 (JP) ........................................ 2000-357456

(51) Int. Cl.[7] .......................... G01N 30/04; B01D 59/44
(52) U.S. Cl. ........................................ 73/23.42; 250/288
(58) Field of Search .......................... 73/23.42; 702/27; 250/288, 282

(56) References Cited

U.S. PATENT DOCUMENTS

| | | | | |
|---|---|---|---|---|
| 3,918,490 A | * | 11/1975 | Goda | 137/597 |
| 4,112,297 A | * | 9/1978 | Miyagi et al. | 250/288 |
| 4,762,995 A | * | 8/1988 | Browner et al. | 250/282 |
| 5,406,079 A | * | 4/1995 | Kato | 250/288 |
| 5,469,369 A | * | 11/1995 | Rose-Pehrsson et al. | 702/27 |

* cited by examiner

*Primary Examiner*—Hezron Williams
*Assistant Examiner*—Jay L. Polizter
(74) *Attorney, Agent, or Firm*—Merchant & Gould P.C.

(57) ABSTRACT

There is provided a gas analyzing apparatus capable of minimizing gas remaining by integrating gas switching apparatuses into one and capable of analyzing impurities of ppb level to sub-ppb level contained in various kinds of high-purity gases efficiently and accurately. The gas analyzing apparatus comprises an analyzer introduction passage 22 for introducing a sample gas supplied from a sample gas source 11 into an analyzer 12 via an analyzer introduction valve 22V; a separator introduction passage 23 diverging from a first side passage of the analyzer introduction valve 22V for introducing a sample gas into a separator 13 via a separator introduction valve 23V; a separator flowing out passage 24 for introducing the sample gas flowing out from the separator 13 into a second side passage of the analyzer introduction valve 22V via a separator flowing-out valve 24V; and a gas switching apparatus to be such formed that when the analyzer introduction valve 22V is opened, the separator introduction valve 23V and the separator flowing-out valve 24V are connectively operated to be closed, and when the analyzer introduction valve 22V is closed, the separator introduction valve 23V and the separator flowing-out valve 24V are connectively operated to be opened.

3 Claims, 2 Drawing Sheets

GAS ANALYZING APPARATUS

BACKGROUND OF THE INVENTION

1. Field of the Invention

The present invention relates to a gas analyzing apparatus, more particularly to a gas analyzing apparatus capable of analyzing impurities of ppb level to sub-ppb level contained in various kinds of high-purity gases with one analyzer.

2. Description of the Prior Art

In a semiconductor-manufacturing field, since trace impurities in high-purity gas to be used have a bad effect on device performance, it is necessary to observe the trace impurities. As a means for analyzing various kinds of impurities of ppb level to ppt level present in high-purity gas, an apparatus has been used recently where a separator such as a gas chromatography or the like and an analyzer such as an atmospheric pressure ionization mass spectrometer (APIMS) are combined.

In the apparatus where the separator and the analyzer are thus combined, for example, as shown in the systematic diagram of FIG. 4, there are cases where a sample gas supplied from a sample gas source 11 is directly analyzed in the analyzer 12, and the sample gas is also analyzed in the analyzer 12 after major components and impurities of the sample gas are separated in a separator 13. In the above apparatus, it is necessary to introduce a sample gas from the sample gas source by switching to the direction of the analyzer 12 and to the direction of the separator 13 in a first gas switching apparatus 14 of a sample gas inlet side, and at the same time, to introduce the sample gas toward the analyzer 12 by switching to the direction of a direct introduction and to the direction of the separator in a second switching apparatus 15 of a sample gas flowing-out side.

That is to say, when the sample gas is directly analyzed in the analyzer 12, a shut off valve 14a is opened and a shut off valve 14b is closed in the first gas switching apparatus 14 while a shut off valve 15a is opened and a shut off valve 15b is closed in the second gas switching apparatus 15. Furthermore, when the analysis of the sample gas is carried out via the separator 13, the shut off valve 14a is closed and the shut off valve 14b is opened in the first gas switching apparatus 14 while the shut off valve 15a is closed and the shut of valve 15b is opened in the second gas switching apparatus 15. Furthermore, when the separator 13 is not used during the analysis, a carrier gas supplied to the separator 13 from a carrier gas source 16 is exhausted to the outside from an exhaust valve 17 provided in an outlet passage of the separator 13.

However, according to the construction as abovementioned, two gas switching apparatuses must be used. Moreover, the opening and closing of the shut off valves of both the gas switching apparatuses are required to connectively operate. Furthermore, when the separator 13 is used, since a gas passage between both the gas switching apparatuses becomes a condition that the sample gas is shut up and stays therein, it is impossible to carry out the gas switching swiftly. Furthermore, there is such an occasion that analysis results are badly influenced by adsorption/desorption of the sample gas components to/from an inner surface of piping.

SUMMARY OF THE INVENTION

Therefore, the object of the present invention is to provide a gas analyzing apparatus capable of minimizing gas remaining by integrating the gas switching apparatuses into one, and capable of analyzing impurities of ppb level to sub-ppb level contained in various kinds of high-purity gases efficiently and accurately with one analyzer.

To achieve the above object, according to the present invention, there is provided a gas analyzing apparatus comprising a separator such as a gas chromatograph or the like for separating gas components and an analyzer such as an atmospheric-pressure ionization mass spectrometer or the like for analyzing gas components, the gas analyzing apparatus comprising: an analyzer introduction passage for directly introducing a; sample gas supplied from a sample gas source into the analyzer via an analyzer introduction valve; a separator introduction passage diverging from a first side passage of the analyzer introduction valve for introducing a sample gas into the separator via a separator introduction valve; a separator flowing-out passage for introducing the sample gas flowing out from the separator into a second side passage of the analyzer introduction valve via a separator flowing-out valve; and a gas switching apparatus to be such formed that when the analyzer introduction valve is opened, the separator introduction valve and the separator flowing-out valve are connectively operated to be closed, and when the analyzer introduction valve is closed, the separator introduction valve and the separator flowing-out valve are connectively operated to be opened.

In particular, according to the gas analyzing apparatus of the present invention, the gas switching apparatus comprises a purge passage to which a first side passage of said separator flowing-out valve and a second side passage of said separator introduction valve are connected via a purge valve which is opened and closed simultaneously with said analyzer introduction valve.

Furthermore, according to the gas switching apparatus of the present invention, the gas switching apparatus is a 4-connected 4-way valve where respective valves and passages thereof are integrally formed.

Furthermore, according to the present invention, there is provided a gas analyzing apparatus comprising a separator such as a gas chromatograph or the like for separating gas components, an analyzer such as an atmospheric-pressure ionization mass spectrometer or the like for analyzing gas components, a sample gas source for supplying a sample gas, and a carrier gas source for supplying a carrier gas into said separator, said gas analyzing apparatus comprising: a gas switching apparatus comprising: an analyzer introduction passage to which a sample gas passage connected to said sample gas source and an analyzer inlet passage connected to said analyzer are connected via an analyzer introduction valve; a separator introduction passage to which said sample gas passage and a separator inlet passage are connected via a separator introduction valve; a separator flowing-out passage to which a separator outlet passage and said analyzer inlet passage are connected via a separator flowing-out valve; and a purge passage to which said separator outlet passage and a separator inlet passage are connected via a purge valve; wherein said gas switching apparatus is such operated that when said sample gas from said sample gas source is directly introduced into said analyzer, said analyzer introduction valve and said purge valve are opened together while said separator introduction valve and said separator flowing-out valve are closed together thereby said sample gas from said sample gas source is directly introduced into said analyzer via said analyzer introduction passage while a carrier gas supplied from said carrier gas source into said separator and flowing out from said separator outlet passage is introduced into said separator inlet passage via said purge passage, and when said sample gas from said sample gas source is introduced into said analyzer after said sample gas is separated in said separator, said analyzer introduction valve and said purge valve are closed together while said separator introduction valve and said separator flowing-out valve are opened together thereby said sample gas from said sample gas source is introduced into said separator through said separator introduction passage to be separated in said separator and then is accompanied by said carrier gas to flow out from said separator outlet passage and then introduced into said analyzer inlet passage through said separator flowing-out passage.

DESCRIPTION OF THE PREFERRED EMBODIMENTS

Figure 1:
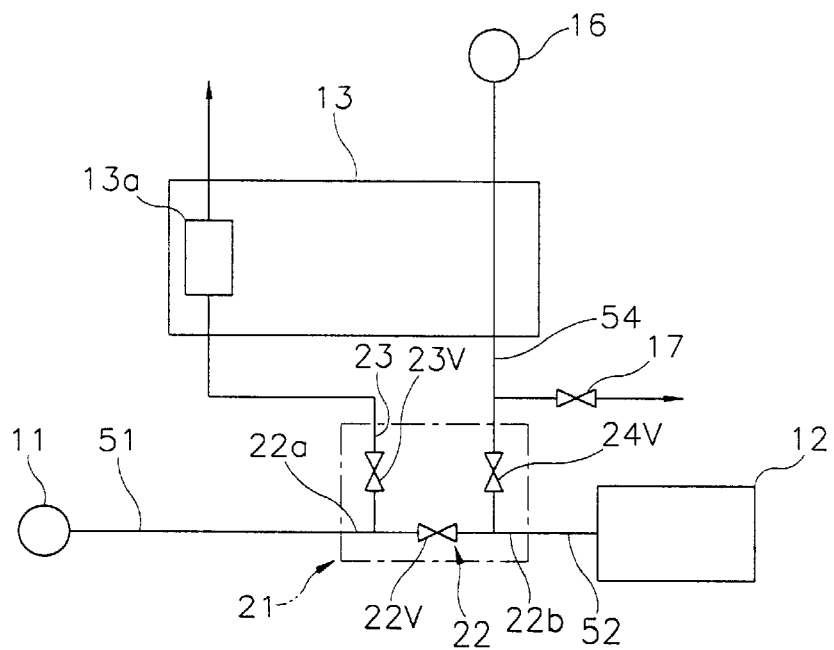
FIG. 1 is a systematic diagram showing the first embodiment of a gas analyzing apparatus according to the present invention.

FIG. 1 is a systematic diagram showing the first embodiment of a gas analyzing apparatus according to the present invention. In the gas analyzing apparatus where a separator 13 such as a gas chromatograph or the like and an analyzer 12 such as an atmospheric-pressure ionization mass spectrometer are combined via a gas switching apparatus 21, an operation to analyze a sample gas supplied from a sample gas source 11 by directly introducing the sample gas to the analyzer 12 and an operation to analyze a sample gas in the analyzer 12 after the sample gas is introduced into the separator 13 for separating gas components thereof, are switched by switching the gas passages of the gas switching apparatus 21.

The gas switching apparatus 21 used in this embodiment is an integrated valve, so called, 3-connected 4-way valve comprising an analyzer introduction passage 22 for directly introducing the sample gas supplied from the sample gas source 11 by a sample gas passage 51 into an analyzer inlet passage 52 connected to the analyzer 12 via an analyzer introduction valve, 22V, a separator introduction passage 23 diverging from a first side passage 22a of the analyzer introduction valve 22V for introducing the sample gas from a separator inlet passage 53 into the separator 13 via a separator introduction valve 23V, a separator flowing-out passage 24 for introducing the gas flowing out from the separator 13 to a separator outlet passage 54 into a second side passage 22b of the analyzer introduction valve 22V via a separator flowing-out valve 24V and then for introducing the gas into the analyzer 12 via the analyzer inlet passage 52.

The gas switching apparatus 21 is such formed that the separator introduction valve 23V and the separator flowing-out valve 24V are simultaneously operated with the analyzer introduction. valve 22V, and such that when the analyzer introduction valve 22V is opened, the separator introduction valve 23V and the separator flowing-out valve 24V are closed together. Furthermore, an exhaust valve 17 for exhausting a carrier gas supplied into the separator 13 from a carrier gas source 16 is provided in the separator outlet passage 54.

When the sample gas is directly analyzed in the analyzer 12, the analyzer introduction valve 22V of the gas switching apparatus 21 is opened. Connectively operating to this, the separator introduction valve 23V and the separator flowing-out valve 24V are closed together and in addition, the exhaust valve 17 is opened. Thus, the sample gas supplied into the gas switching apparatus 21 from the sample gas source 11 passes through the analyzer introduction valve 22V and is introduced into the analyzer 12 from the analyzer inlet passage 52 via the analyzer introduction passage 22, thereby a predetermined analyzing operation is carried out in the analyzer 12. At this time, the carrier gas supplied into the separator 13 and flowing out into the separator outlet passage 54 is exhausted into the outside from the exhaust valve 17.

Furthermore, when the analysis is carried out in the analyzer 12 after gas components are separated in the separator 13, the analyzer introduction valve 22V and the exhaust valve 17 are closed. Connectively operating, the separator introduction valve 23V and the separator flowing-out valve 24V are opened together. Thus, the sample gas supplied from the sample gas source 11 passes through the separator introduction valve 23V and is introduced into the separator 13 from the Separator introduction passage 23 via the separator inlet passage 53, thereby the sample gas is measured in a sampling portion 13a of the separator 13. After a predetermined separating operation is carried out in a separating column provided in the separator 13, the measured sample gas is accompanied by a predetermined amount of the carrier gas supplied from the carrier gas source 16 to be introduced into the separator outlet passage 54 from the separator 13 and then, introduced into the second side passage 22b of the analyzer introduction valve 22V through the separator flowing-out valve 24V of the separator flowing-out passage 24 to thereby be introduced into the analyzer 12 via the analyzer inlet passage 52. In the gas switching apparatus 21 thus formed, since only one analyzer introduction valve 22V is provided in the analyzer introduction passage 22 to be used in the direct analysis, even though the analyzer introduction valve 22V is closed when the sample gas is separated in the separator 13, there is no case where the sample gas is shut up and stays, and adsorption/desorption of the remaining gas does not occur. Therefore, it is possible to accurately and swiftly carry out a continuous measurement by gas switching. Furthermore, it is possible to obtain a simple, space-saving and low-cost gas switching apparatus be decreasing the number of valves compared to the conventional apparatus.

Figure 2:
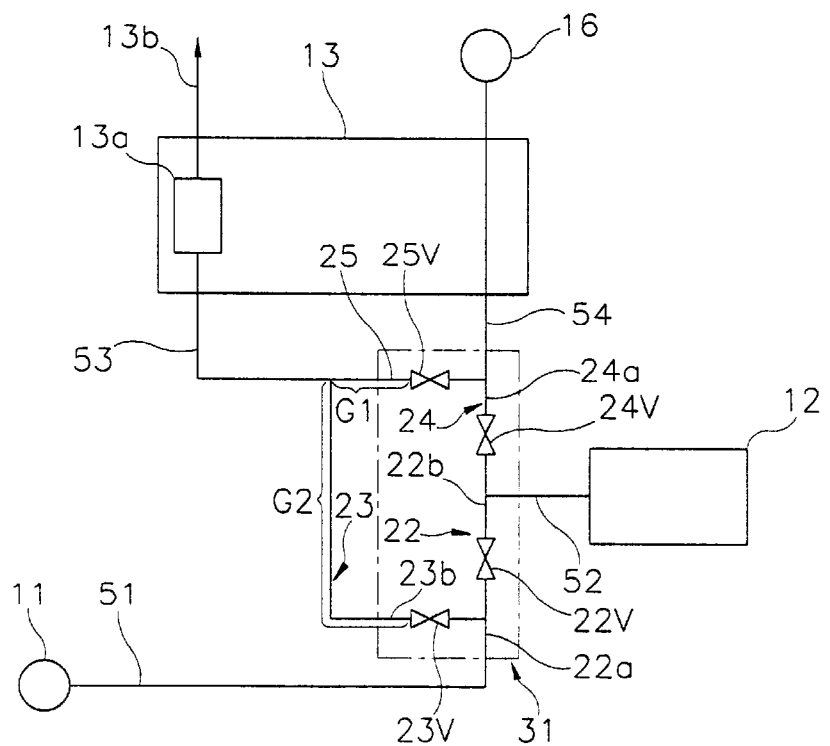
FIG. 2 is a is a systematic diagram showing the second embodiment of the gas analyzing apparatus according to the present invention.

FIG. 2 is a systematic diagram showing the second embodiment of the gas analyzing apparatus according to the present invention, which uses a carrier gas (the gas exhausted into the outside in the first embodiment) as a purge gas of the separator 13. In addition, the same reference numerals will be used for the same elements as in the first embodiment in the following explanation, and the detailed description thereabout will be omitted.

That is to say, similarly to the first embodiment, in addition to the analyzer introduction passage 22 having the analyzer introduction valve 22V and the separator introduction passage 23 having the separator introduction valve 23V and the separator following-out passage 24 having the separator flowing-out valve 24V, a gas switching apparatus 31 to be used in this embodiment is formed so that a first side passage 24a of the separator flowing-out valve 24V and a second side passage 23b of the separator introduction valve 23V are connected to a purge passage 25 having a purge valve 25V which is opened and closed simultaneously with the analyzer introduction valve 22V.

When the sample gas is directly analyzed in the analyzer 12, the analyzer introduction valve 22V and the purge valve 25V are opened together and the separator introduction valve 23V and the separator flowing-out valve 24V are closed together. Since the separator flowing-out valve 24V is closed, the carrier gas supplied from the carrier gas source 16 flows from the first side passage 24a into the purge passage 25 and is introduced into the second side passage 23b of the separator introduction valve 23V through the purge valve 25V. Since the separator introduction valve 23V is closed, the carrier gas is introduced from the separator introduction passage 23 into the separator 13 and then, exhausted into the outside from an exhaust passage 13b through the sampling portion 13a.

Furthermore, when the analysis is carried out by using the separator 13, the analyzer introduction valve 22V and the purge valve 25V are closed and the separator introduction valve 23V and the separator flowing-out valve 24V are opened. The sample gas from the sample gas source 11 passes through the separator introduction valve 23V and is introduced from the separator introduction passage 23 into the separator 13 to be measured in the sampling portion 13a. After a predetermined separating operation is carried out, the sample gas is accompanied by the carrier gas from the carrier gas source 16 to flow out from the separator 13 and is introduced into the second side passage 22b of the analyzer introduction valve 22V through the separator flowing-out valve 24V of the separator flowing-out passage 24 and then, introduced into the analyzer 12 via the analyzer introduction passage 22.

Therefore, when the analysis is carried out by using the separator 13, the sample gas flows into a passage including the sampling portion 13a of the separator 13, and when the sample gas is directly analyzed in the analyzer 12 without using the separator 13, the carrier gas is made to flow into the passage 22b. That is to say, a gas which is not introduced into the analyzer 12 is always made to flow into the sampling portion 13a of the separator 13. There is no case where the sampling gas remains in the passage including the sampling portion 13a. Furthermore, it is possible to securely prevent air from flowing backward to the sampling portion 13a from the exhaust passage 13b via an exhaust piping. Moreover, there becomes is no case where the sampling portion 13a or an inside of a passage reaching thereto is contaminated by remaining gas or air.

Thus, it is possible to accurately and swiftly carry out the continuous measurement by gas switching. At this time, even though all the gas remaining portions are not minimized in the respective passages in the gas switching apparatus 31, it is preferable that a gas remaining portion G1 when the sample gas flows from the separator introduction valve 23V into the sampling portion 13a is made smaller. Even though a gas remaining portion G2 when the carrier gas flows into the sampling portion 13a is made relatively larger, the analysis is little affected by this.

Figure 3:
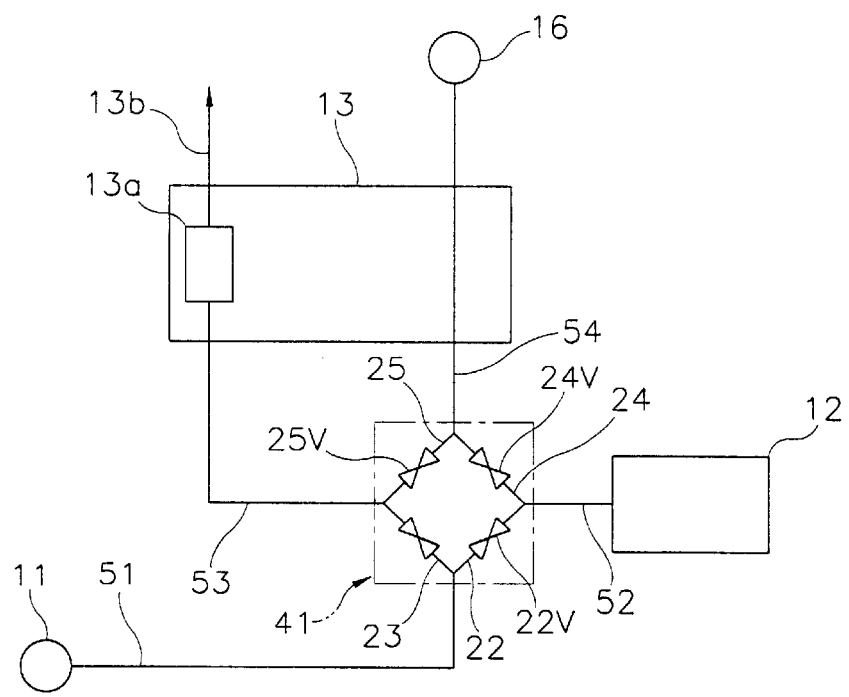
FIG. 3 is a systematic diagram showing the third embodiment of the gas analyzing apparatus according to the present invention.
Figure 4:
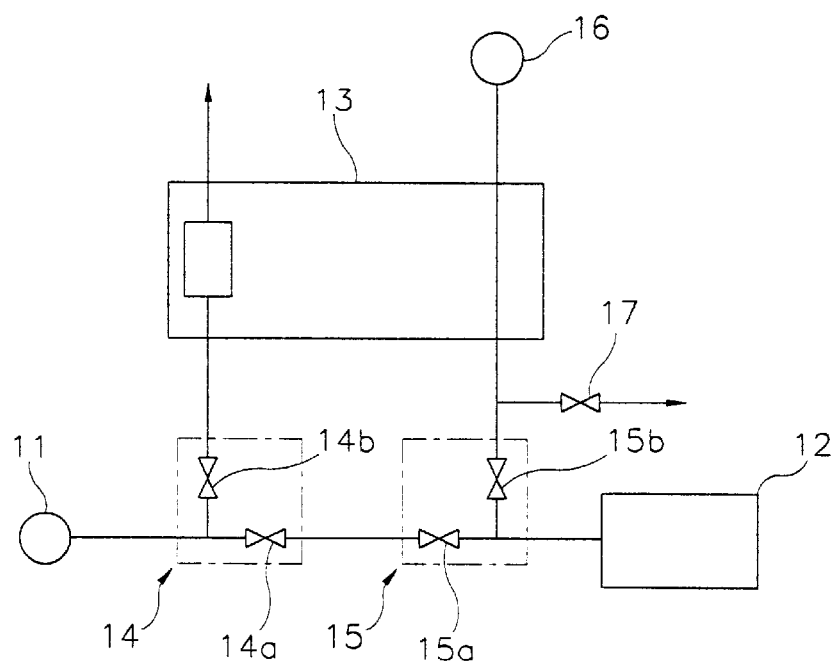
FIG. 4 is a systematic diagram showing a conventional analyzing apparatus where a separator and an analyzer are combined.

FIG. 3 is a systematic diagram showing the third embodiment of the gas analyzing apparatus according to the present invention. Similar to the gas switching apparatus 31 shown in the above second embodiment, a gas switching apparatus 41 shown in this embodiment comprises the analyzer introduction passage 22 having the analyzer introduction valve 22V, the separator introduction passage 23 having the separator introduction valve 23V, the separator flowing-out passage 24 having the separator flowing-out valve 24V, and the purge passage 25 having the purge valve 25a. In the gas switching apparatus 41 of this embodiment, the arrangement of the respective valves is designed such that the connecting portions of the respective passages become shortest.

That is to say, by arranging the respective valves at an equal distance and at an angle of 90° and making junctions of the respective passages in the gas switching apparatus 41 to come as close to the valves as possible, gas remaining portions when the opening and closing of the valves are switched are made to be minimized.

By minimizing-all the gas remaining portions like this, even when plural kinds of the sample gases are switched to be analyzed, it is possible to prevent a sample gas of the previous analysis from being detected as impurity in the next analysis of another sample gas.

For example, in the gas switching apparatus 41 of the third embodiment, assume the sample gas is oxygen and the carrier gas is helium and impurities in oxygen are analyzed. At first, in the initial state of the gas switching apparatus 41, since the separator introduction valve 23V and the separator flowing-out valve 24V are opened and the analyzer introduction valve 22V and the purge valve 25V are closed, oxygen as the sample gas from the sample gas source 11 flows into the gas switching apparatus 41 and passes through the separation introduction valve 23V and then, flows from the separator introduction passage 23 into the separator 13 to thereby be introduced into the sampling portion 13a. At this time, helium as the carrier gas supplied from the carrier gas source 16 to the separator 13 is introduced into the analyzer 12 from the separator flowing-out passage 24 through the separator flowing-out valve 24V.

The impurities to be analyzed, which are contained in the sample gas sampled in the sampling portion 13a and are separated in the separator 13, are accompanied by the carrier gas to flow out from the separator 13 and pass through the separator flowing-out valve 24V of the gas switching apparatus 41 and then, are introduced into the analyzer 12 from the separator flowing-out passage 24 to thereby be analyzed.

Next, the gas switching operation is carried out. That is to say, the separator introduction valve 23V and the separator flowing-out valve 24V of the gas switching apparatus 41 are closed and at the same time, the analyzer introduction valve 22V and the purge valve 25V are opened. Thus, oxygen from the sample gas source 11 passes through the analyzer introduction valve 22V and is introduced into the analyzer 12 from the analyzer introduction passage 22, thereby impurities in oxygen are directly analyzed. At this time, helium flowing out from the separator 13 flows toward the sampling portion 13a through the purge valve 25V to thereby be exhausted form the exhaust passage 13b.

Therefore, since any one of oxygen as the sample gas or helium as the carrier gas is continuously supplied into the analyzer 12 and the separator 13 without stopping, it is possible to avoid contamination due to the back flow of the air to the sampling portion 13a or adsorption/desorption due to the gas remaining.

At this time, even though the gas remaining portions of the gas switching apparatus 31 shown in the second embodiment are larger than those of the gas switching apparatus 41 shown in the third embodiment, since the flowing carrier gas is not an impurity to be analyzed which is capable of having a bad effect on the analysis but rather is a gas for which it is difficult to have an effect on the analysis and aims at a page of the passage including the sampling portion 13a, an effect on the analysis of the gas remaining portions is minimized in the gas switching apparatus 31.

By returning to the initial state after finishing the direct analysis of oxygen, it is possible to carry out the analysis again by using the separator 13. Thus, by controlling the respective shut off valves of the gas switching apparatus, it is possible to carry out the gas switching between the direct analysis and the separating analysis of the sample gas accurately and swiftly.

As described above, according to the gas analyzing apparatus of the present invention, it is possible to effectively, swiftly and securely carry out the operation to directly analyze impurities in the sample gas, and the operation to analyze them after separating major components and impurities by using the separator such as a gas chromatograph or the like, with one analyzing apparatus. Furthermore, since the introduction passage of the sample gas is one, it is possible to calibrate for the direct introduction analysis and the separating analysis with one calibration apparatus.

What is claimed is:

1. A gas analyzing apparatus comprising a separator such as a gas chromatograph or the like for separating components and an analyzer such as an atmospheric-pressure ionization mass spectrometer or the like for analyzing gas components, said gas analyzing apparatus further comprising:

an analyzer introduction passage for directly introducing a sample gas supplied from a sample gas source into said analyzer via an analyzer introduction valve;

a separator introduction passage diverging from a first side passage of said analyzer introduction valve for introducing said sample gas into said separator via a separator introduction valve;

a separator flowing-out passage for introducing at least some of said sample gas flowing out from said separator into a second side passage of said analyzer introduction valve via a separator flowing-out valve; and a valve for blocking or passing carrier gas supplied from a carrier gas source;

wherein, when said analyzer introduction valve and said blocking or passing carrier gas valve are operated to be opened, said separator introduction valve and said separator flowing-out valve are connectively operated to be closed, and when said analyzer introduction valve and said blocking or passing carrier gas valve are operated to be closed, said separator introduction valve and said separator flowing-out valve are connectively operated to be opened.

2. The gas analyzing apparatus of claim 1, wherein said gas switching apparatus comprises:

a purge passage to which a first side passage of said separator flowing-out valve and a second side passage of said separator introduction valve are connected via said blocking or passing carrier gas valve.

3. The gas analyzing apparatus of claim 1 wherein said analyzer introduction valve, said separator introduction valve, said separator flowing-out valve and said blocking or passing carrier gas valve are formed as a 4-connected 4-way valve.

* * * * *